United States Patent
Paulsen et al.

(10) Patent No.: US 12,161,510 B2
(45) Date of Patent: Dec. 10, 2024

(54) MEASURING CHORDAE TENDINEAE FORCES USING FIBER BRAGG GRATING OPTICAL FORCE SENSORS

(71) Applicant: The Board of Trustees of the Leland Stanford Junior University, Stanford, CA (US)

(72) Inventors: Michael John Paulsen, Los Altos, CA (US); Y. Joseph Woo, Menlo Park, CA (US); Mark R. Cutkosky, Palo Alto, CA (US); Jung Hwa Bae, Millbrae, CA (US); Annabel M. Imbrie-Moore, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 700 days.

(21) Appl. No.: 17/266,918

(22) PCT Filed: Aug. 28, 2019

(86) PCT No.: PCT/US2019/048571
§ 371 (c)(1),
(2) Date: Feb. 8, 2021

(87) PCT Pub. No.: WO2020/047096
PCT Pub. Date: Mar. 5, 2020

(65) Prior Publication Data
US 2021/0338364 A1    Nov. 4, 2021

Related U.S. Application Data

(60) Provisional application No. 62/723,949, filed on Aug. 28, 2018.

(51) Int. Cl.
A61B 90/00    (2016.01)
A61F 2/24    (2006.01)
G01L 1/24    (2006.01)

(52) U.S. Cl.
CPC ............ *A61B 90/06* (2016.02); *A61F 2/2457* (2013.01); *G01L 1/246* (2013.01); *A61B 2090/064* (2016.02)

(58) Field of Classification Search
CPC .............. A61B 90/06; A61B 2090/064; A61B 2562/0266; G01L 1/246; A61F 2/2457
See application file for complete search history.

(56) References Cited

U.S. PATENT DOCUMENTS 6,337,737 B1 *  1/2002  Chang ................ G01D 5/35316
                                                    385/12
8,121,687 B2   2/2012  Jensen
(Continued)

OTHER PUBLICATIONS

He, Z., and Jowers, C. (Nov. 20, 2008). "A Novel Method to Measure Mitral Valve Chordal Tension." ASME. J Biomech Eng. Jan. 2009; 131(1): 014501. https://doi.org/10.1115/1.3005160 (Year: 2008).*

(Continued)

*Primary Examiner* — Yi-Shan Yang
*Assistant Examiner* — Kyle W. Kretzer
(74) *Attorney, Agent, or Firm* — Lumen Patent Firm

(57) ABSTRACT

Fiber Bragg grating (FBG) sensors are used to provide measurement of chordae tendineae forces. Two basic modes of operation are considered, The first mode is a research mode, where the FBG sensors are affixed to native chordae in situ and preferably in vivo to provide data on chordae forces in a beating heart under various conditions (e.g., normal, hypertensive, etc.), The second mode is a clinical mode, where the FBG sensor can be used to measure tension (Continued)

on a prosthetic neochord during the surgical procedure to implant the prosthesis.

12 Claims, 12 Drawing Sheets

(56) References Cited

U.S. PATENT DOCUMENTS

| | | | |
|---|---|---|---|
| 8,989,528 B2 | 3/2015 | Udd | |
| 2003/0105519 A1* | 6/2003 | Fasol | A61F 2/2457 606/228 |
| 2016/0262627 A1* | 9/2016 | Hecker | A61B 5/205 |
| 2019/0159686 A1* | 5/2019 | Bak-Boychuk | A61B 5/1114 |

OTHER PUBLICATIONS

Henrik Jensen, et al. "Transapical neochord implantation: Is tension of artificial chordae tendineae dependent on the insertion site?", J Thorac Cardiovasc Surg. Jul. 2014; 148(1):138-43. doi: 10.1016/j.jtcvs.2013.07.068. Epub Sep. 14, 2013. PMID: 24041766. (Year: 2014).*

Nielsen SL, Soerensen DD, Libergren P, Yoganathan AP, Nygaard H. Miniature C-shaped transducers for chordae tendineae force measurements. Ann Biomed Eng. Aug. 2004;32(8):1050-7. doi: 10.1114/b:abme.0000036641.69903.62. PMID: 15446501. (Year: 2004).*

Ostli B, et al. "In Vitro System for Measuring Chordal Force Changes Following Mitral Valve Patch Repair". Cardiovasc Eng Technol . Sep. 2012;3(3):263-268. doi: 10.1007/s13239-012-0098-2. PMID: 26273417; PMC4532353. (Year: 2012).*

Grinberg et al., "Measuring chordae tension during transapical neochordae implantation: Toward understanding objective consequences of mitral valve repair", Nov. 2018, J Thoracic and Cardiovascular Surg 158(3).

Grinberg et al., "Mitral valve repair based on intraoperative objective measurement", 2019, Scientific Reports 9:4677.

Ho et al. FBM Sensor for Contacrt Level Monitoring and Prediction of Perforation in Cardiac Ablation. Sensors 2012, 12, 1002-1013.

Abushagur et al. Advances in Bio-Tactile Sensors for Minimally Invasive Surgery Using the Fibre Bragg Grating Force Sensor Technique: A survey. Sensors 2014, 14, 6633-6665.

\* cited by examiner providing a fiber Bragg grating (FBG) force sensor having a first attachment point and a second attachment point, wherein the FBG force sensor is configured to sense tensile force applied to pull the first and second attachment points apart

affixing the first attachment point of the FBG force sensor to a chordae tendineae at a first location on the chordae tendineae

affixing the second attachment point of the FBG force sensor to the chordae tendineae at a second location on the chordae tendineae

wherein a sensor distance between the first and second attachment points is substantially the same as a chordae distance between the first and second locations

cutting the chordae tendineae between the first and second locations

performing force measurements with the FBG force sensor during operation of a heart valve connected to the chordae tendineae

FIG. 9

MEASURING CHORDAE TENDINEAE FORCES USING FIBER BRAGG GRATING OPTICAL FORCE SENSORS

FIELD OF THE INVENTION

This invention relates to the use of fiber Bragg grating sensors to measure chordae tendineae forces, both for research applications and in surgical procedures.

BACKGROUND

Chordae tendineae are tendon-resembling fibrous cords of connective tissue that connect the papillary muscles to the tricuspid valve and the bicuspid valve (i.e., mitral valve) in the heart. Measuring the forces present in chordae tendineae in situ and preferably in vivo is desirable to improve understanding of heart valve function, which may lead to improved heart valve surgical procedures. However, it is difficult to measure forces in chordae tendineae in situ and especially in vivo with conventional approaches, as described in greater detail below. Accordingly, it would be an advance in the art to provide improved measurement of chordae tendineae forces.

SUMMARY

In this work, fiber Bragg grating (FBG) sensors are used to provide measurement of chordae tendineae forces. Two basic modes of operation are considered. The first mode is a research mode, where the FBG sensors are affixed to native chordae in situ and preferably in vivo to provide data on chordae forces in a beating heart under various conditions (e.g., normal, hypertensive, etc.). The second mode is a clinical mode, where the FBG sensor can be used to measure tension on a prosthetic neochord during the surgical procedure to implant the prosthesis.

BRIEF DESCRIPTION OF THE DRAWINGS

FIG. 9 shows an exemplary embodiment of the invention.

DETAILED DESCRIPTION

Figure 1A:
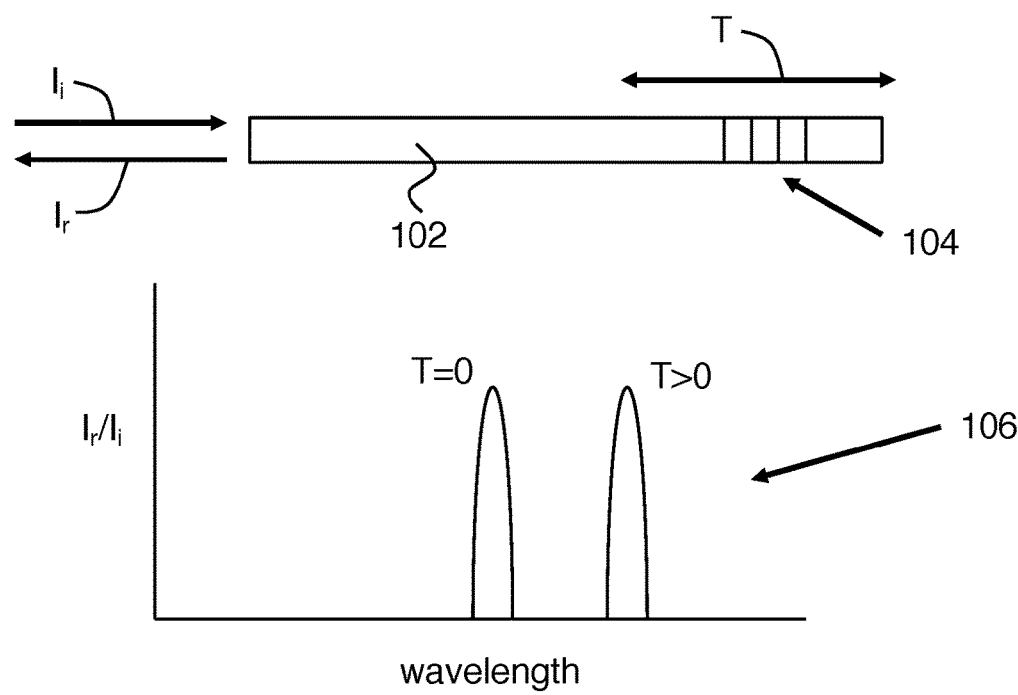
FIG. 1A shows the operating principle of a fiber Bragg grating sensor.

Section A describes general principles relating to embodiments of the invention. Section B provides a detailed description of experimental work on the use of fiber Bragg grating sensors to sense chordae tendineae forces. Section C describes further embodiments and variations.

A) General Principles

An embodiment of the invention is a method of measuring chordae tendineae forces during operation of a heart valve. The method includes the steps of:
1) providing a fiber Bragg grating (FBG) force sensor having a first attachment point and a second attachment point, where the FBG force sensor is configured to sense tensile force applied so as to pull the first and second attachment points apart;
2) affixing the first attachment point of the FBG force sensor to a chordae tendineae at a first location on the chordae tendineae;
3) affixing the second attachment point of the FBG force sensor to the chordae tendineae at a second location on the chordae tendineae—here a sensor distance between the first and second attachment points is substantially the same as a chordae distance between the first and second locations;
4) cutting the chordae tendineae between the first and second locations; and
5) performing force measurements with the FBG force sensor during operation of a heart valve connected to the chordae tendineae. Such force measurements can be done in situ (e.g., in a left heart simulator) or in vivo (e.g., in an experimental animal).

Here a fiber Bragg grating (FBG) sensor is an optical fiber having a Bragg grating in it. Strain in the optical fiber changes the period of the grating, thereby affecting its reflectance (or transmittance) spectrum. Calibration of the force-optical characteristics of an FBG sensor provides an FBG force sensor.

Preferably, the heart valve is a mitral valve. The FBG force sensor is preferably configured to provide a reflectance spectrum from which force is determined (as opposed to operating in a transmittance mode).

The FBG force sensor is preferably surrounded by a protective sheath. This protective sheath can include several layers. In one example, the protective sheath includes a coil affixed to the FBG force sensor at the first and second attachment points and having a separation between adjacent coil loops sufficient to accommodate a suture.

The protective sheath can include a urethane shell disposed circumferentially around the FBG force sensor and bonded to the FBG force sensor. This example can further include a coil disposed circumferentially around and in contact with the urethane shell. The protective sheath can further include heat shrink tubing disposed circumferentially around and in contact with the coil along part of a length of the FBG force sensor. The resulting exposed part of the coil can provide suture locking grooves.

Preferably, the protective sheath is configured to reduce non-tensile force on the FBG force sensor. Practice of the invention does not depend critically on the material in which the FBG sensor is fabricated. Silica fibers are used in the experiments described below, while polymer fibers are expected to be less fragile.

An important aspect of the sensors of this work is that they can be made small. For example, a distance between the first and second attachment points can be 10 mm or less Another embodiment of the invention is a FBG force sensor configured for use as a chordae tendineae force sensor. Here the FBG force sensor includes:
1) an optical fiber having a grating in it;
2) a urethane shell disposed circumferentially around the optical fiber and bonded to the optical fiber;
3) a coil disposed circumferentially around and in contact with the urethane shell; and
4) heat shrink tubing disposed circumferentially around and in contact with the coil along part of a length of the FBG force sensor.

Here also, practice of the invention does not depend critically on the material in which the FBG sensor is fabricated. Silica fibers are used in the experiments described below, while polymer fibers are expected to be less fragile. Also as above, the exposed part of the coil (i.e., not covered by the heat shrink tubing) can provide suture locking grooves.

Another embodiment of the invention is a method of heart valve surgery. Here the method includes:
1) providing a prosthetic artificial neochordae;
2) anchoring a heart valve leaflet to a heart wall with the prosthetic artificial neochordae with a surgical procedure;
3) providing a fiber Bragg grating sensor affixed to the prosthetic artificial neochordae during the surgical procedure and configured to measure tensile force on the prosthetic artificial neochordae; and
4) monitoring tensile force on the prosthetic artificial neochordae during the surgical procedure using the fiber Bragg grating sensor.

B) Fiber Bragg Grating Sensors for Measuring Chordae Tendineae Forces

B1) Introduction

In the United States, valvular heart disease is a common cause of morbidity and mortality, with an estimated 2.5% of the population affected. In large epidemiologic natural history studies, projected 5- and 8-year survival rates for individuals suffering from valvular heart disease is 79% and 68% respectively, rivaling that of many types of cancer. The most prevalent type of valvular heart disease is degenerative or myxomatous mitral regurgitation, with nearly 2% of the US population suffering from at least moderate mitral regurgitation. Of these patients, approximately 10% progress to severe mitral regurgitation requiring surgery. Mitral valve repair is the preferred treatment for degenerative mitral regurgitation. As compared to valve replacement with a bioprosthetic or mechanical valve, an effective and durable mitral valve repair procedure improves patient survival, preserves left ventricular function, and results in greater freedom from reoperation. However, the key part of this statement is "effective and durable" as many surgeons lack the knowledge or ability to perform this type of repair; as such, a large subset of patients with degenerative mitral disease still undergo replacement over repair.

The mitral valve apparatus is a dynamic and intricate structure that is comprised of two leaflets (anterior and posterior); the atriovalvular junction and annulus connecting the leaflets to the walls of the heart; and the subvalvular apparatus. The subvalvular apparatus consists of long fibrous supports called chordae tendineae, which anchor the leaflets to the papillary muscles and left ventricular free wall. Dysfunction of any of these components can result in valve incompetence and resultant mitral regurgitation. To succeed in repairing a dysfunctional mitral valve, a comprehensive understanding of the mitral valve apparatus spatial geometry is mandatory. Even with this knowledge, however, mitral valve repair is challenging and our understanding of how exactly the mitral valve functions is incomplete. Clouding this further is the existence of a multitude of mitral repair techniques, with little to no consensus or objective physiological data suggesting which repair technique is superior. The ability to quantitatively measure structural data, such as chordae tendineae tension, without adversely impacting leaflet motion, would generate a more comprehensive understanding of mitral valve pathology and how best to treat it.

Very few technologies exist that can provide quantitative data on forces within the mitral valve complex. Echocardiography can generate extremely useful, and increasingly high-fidelity, estimates of strain and forces within the mitral valve apparatus, but may be limited by tissue penetration and the inability to make direct measurements. Although marker-based strain measurements can be performed to analyze the chordae tendineae, the narrow thickness and small strains relative to the spatial resolution of the current marker-based optical technology may present significant sources of error, particularly for the primary chordae. Additionally, the restricted optical access and branching patterns of the chordae limits the utility of this technique in vivo. While advancements in machine vision technology and image processing algorithms have made automated analysis of marker-based optical strain measurements substantially faster and more reliable, manual correction and verification remains necessary and time consuming. Small C-shaped force transducers have been described and used to measure transverse chordae tendineae tension both in vitro and in vivo. These transducers have been shown to be reliable and provide high-quality data. A potential limitation, however, is their relatively large footprint relative to the size of the chordae tendineae, which minimizes the number of chordae that may be instrumented simultaneously. Additionally, the transducers have a high mass relative to the chordae, which might interfere with normal chordal motion. The use of miniaturized arthroscopically implantable force probes (AIFP4) for measuring chordal forces has also been described, whereby a small slit is made in the chordae and the elliptical sensor is inserted perpendicularly to measure transverse strain through a cantilever-type mechanism. While this method minimizes the sensor footprint, measurement errors can occur if the sensor shifts from perpendicular alignment. In addition, this technique also requires that a slit large enough to accommodate the 1.8 mm diameter sensor be made in the chordae longitudinally, which limits sensor implantation to only larger chordae. Lastly, these force sensors are no longer available commercially. In this section, we describe the use of Fiber Bragg Grating (FBG) sensors—optical strain gauges made of 125 µm diameter silica fibers—to overcome some limitations of previous methods for measuring chordae tendineae forces.

B2) Methods

B2a) Force-Sensing Neochord

We developed a force-sensing neochord (FSN) that mimics the natural shape and movement of natural chordae tendineae as much as possible to overcome some limitations of prior chordae force transducers. The force-sensing neochord includes an optical strain gauge and attachment method. We chose to use Fiber Bragg Grating (FBG) sensors to measure forces in our force-sensing neochord.

B2a1) Fiber Bragg Grating Optical Strain Sensors

Fiber Bragg Grating sensors are a type of optical strain gauge. When a spectrum of light passes through the optical fiber, the FBG sensor reflects a specific wavelength of light depending on the spatial period of gratings (FIG. 1A). When force is applied on the sensor, the sensor portion of the optical fiber is strained, increasing the distance between gratings. Force-induced strain of the FBG sensor is then detected as a wavelength shift. More specifically, FIG. 1A shows a fiber 102 including a Bragg grating 104 in it. The reflectance $I_r/I_i$ vs. wavelength is schematically shown by 106 on FIG. 1A. Bragg gratings like 104 provide a narrow peak of high reflection and, as indicated above, when the fiber 102 is under tension T the spacing between grating features increases, thereby shifting the wavelength of peak reflection to longer wavelengths, as shown on 106 of FIG. 1A.

Temperature change can also cause a wavelength shift as shown in the following equation:

$$\Delta\lambda = K_\varepsilon \varepsilon + K_T \Delta T \qquad (1)$$

where $\Delta\lambda$ is the wavelength shift, $K_\varepsilon$ is the constant for mechanical strain, $\varepsilon$ is mechanical strain, $K_T$ is the constant for temperature, and $\Delta T$ is the change in temperature. The optical fiber with embedded FBG sensors is waterproof, facilitating implementation of the chordae in a fluid-filled test chamber while the interrogator that reads the wavelength can remain outside of the chamber. Additionally, FBG sensors are very sensitive to mechanical strain; the minimum strain the sensor can resolve is approximately 0.1 μstrain.

B2a2) Design and Fabrication of the Force-Sensing Neochord

Figures 1B, 1C:
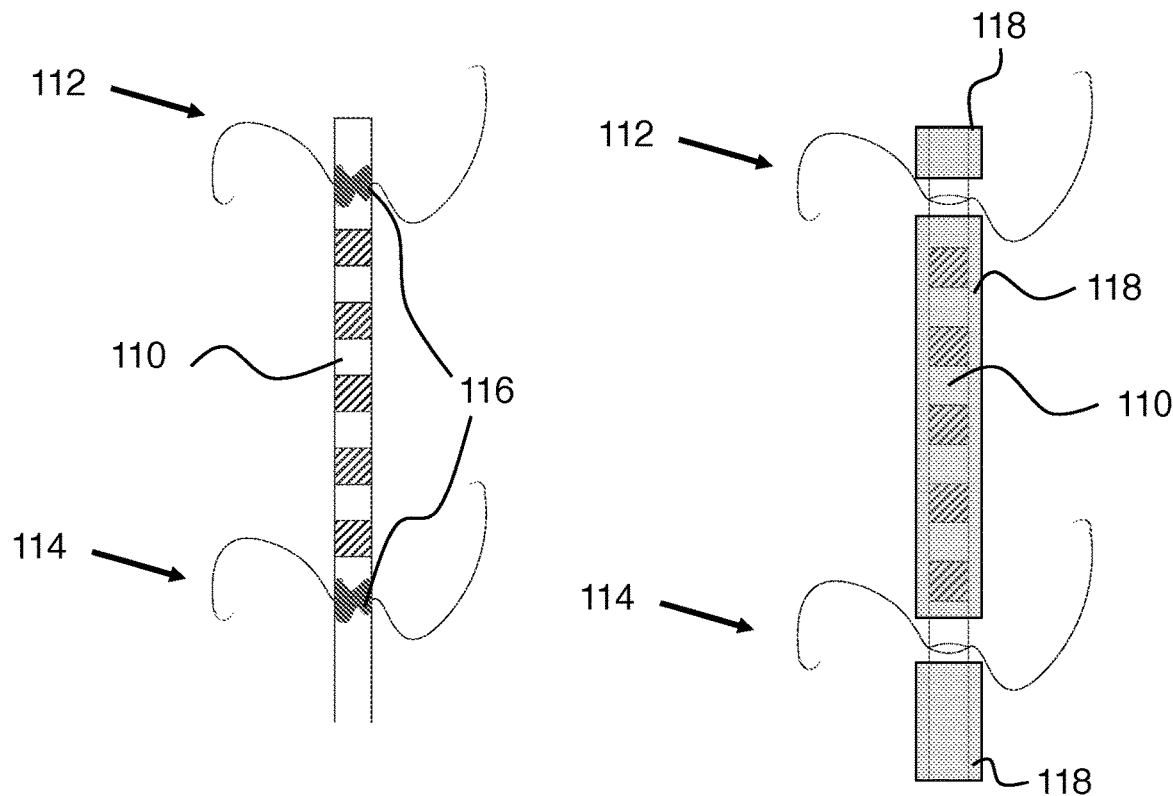
FIGS. 1B-D show exemplary fiber Bragg grating sensors configured to measure chordae tendineae forces.
Figure 1D:
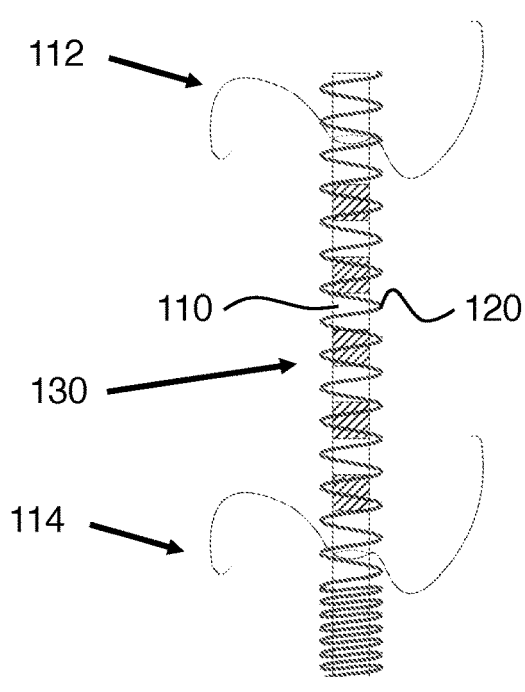

Unlike foil strain gauges, FBG sensors can be used without any base structure to attach the strain gauges. The FBG sensor fiber (DTG-LBL-1550 125 μm FBGS International, Belgium) can be the base structure itself, as it is strong enough to sustain newtons of tensile force. With no base structure, we can achieve maximum force sensitivity from the FBG sensor as well as a lightweight and compact final sensing unit that reduces noise due to inertia of the base structure in dynamic force reading. Various prototype sensor iterations are shown in FIGS. 1B-D.

In our first iteration (FIG. 1B), we tied and glued two double-armed polytetrafluoroethylene sutures (Gore-Tex® CV-7 Suture, W. L. Gore & Associates Inc., Flagstaff, Arizona, United States), 112 and 114 just proximal and distal to the 8 mm FBG sensor 110 using cyanoacrylate 116. Two square knots were tied prior to gluing and demonstrated secure bonding up to 4 N. The sutures 112 and 114 were then used to secure the sensor to the chordae tendineae of interest with great care taken to ensure that the native length was preserved and not affected by sensor implantation. Nonetheless, small imperfections in the resultant length of the instrumented chordae represent a limitation of this model given that changes in chordal length could affect the measured loads.

First, the proximal suture was attached to the chordae distal to the chordae's papillary muscle insertion; any bunching or stretching of the chord due to small misalignments (which could ultimately affect the final length of the instrumented chordae) were corrected by shifting the FBG up or down to return the chordae to its native state. The other end of the FBG sensor was then attached to the chordae proximal to the leaflet insertion point and the chordae was severed between attachment points, loading the forces to the sensor. It was important to leave some length of chordae intact proximally and distally to the fiber attachment points to retain the material properties of the chordae, given that the elastic modulus of the fiber sensor is several hundred times greater than that of a typical chordae.

Initially, the FBGs were manufactured to be 8 mm in length, though we eventually reduced this length to 3 mm overall; as the length decreases and the sensor replaces a smaller section of the chordae, the stiffness of the instrumented chordae converges to the native stiffness. The effect of fiber stiffness relative to chordae stiffness, and its effect on sensor error, is discussed more fully in the Error Estimation section below. While the first prototype performed extremely well, a critical limitation was the difficulty in reusing the fibers for subsequent experiments. To do so, it was necessary to dissolve the glue and then re-tie and re-glue the sutures; this was a laborious process and required great care to avoid breaking the fibers.

To make the sensors easier to reuse, flanges on each end of the FBG sensor were fashioned from 900 μm plastic furcation tubing 118, which was then glued to the fiber, leaving small gaps proximal and distal to the sensor, as shown in FIG. 1C. These flanges served as suture-locking grooves, achieving a similar suture attachment without the use of glue. In this design, the PTFE suture sewn to the chordae was tied between the flanges within the suture-locking groove, which kept the fiber securely in place. Depending on the diameter of the chordae, various sizes of PTFE suture can be used, ranging from size CV-5 to CV-7 in these experiments. After the experiment, the suture was cut and easily removed without damaging the sensor. This modified design successfully allowed us to reuse the sensors multiple times, but also possessed limitations. The bare optical fiber was exposed in the flanges between the furcation tubing, creating a fragile point in the sensor that tended to get caught in the papillary muscle holding mechanism during removal, often resulting in fiber damage.

In our final prototype FSN 130 on FIG. 1D, we kept the suture-locking groove method for attaching the sensors to the chordae for easy reuse, but fashioned the grooves from a different material—a small 0.025" outer diameter flat coil 120, as shown in FIG. 1D. For early prototypes, we used the outer coil of a vascular access wire, in this case a 0.025" Amplatz Extra-Stiff™ guidewire (Cook Medical, Bloomington, Indiana, United States) which consists of a stainless-steel mandrel covered in a PTFE-coated stainless-steel flat coil. Each end of the wire was cut so that the mandrel could be removed, leaving only the hollow outer coil. On one end, the coil was expanded, creating gaps between the wires. The length of the expanded section was trimmed to 12 mm to accommodate 2 mm for suture attachment on each end of the 8 mm FBG; once the 3 mm FBGs were manufactured, total length of the expanded section was reduced to approximately 7 mm. The FBG fiber, which was prepared beforehand by terminating the fiber 2 mm distal to the end of the FBG, was then carefully passed through the non-expanded end of the coil until it was flush with the expanded end of the coil. Cyanoacrylate glue was used to securely bond the FBG to the outer coil, being careful not to use an excessive amount of glue that would fill the gaps between the coil and render it useless as a flange to retain suture. The FSN was attached to the mitral valve chordae in a similar fashion as described in the prior section for the flanged prototype. Further iterations have used customized flat coils with features specific to this implementation as well as an optimized implantation protocol described below.

B2a3) Calibration

Figure 1E:
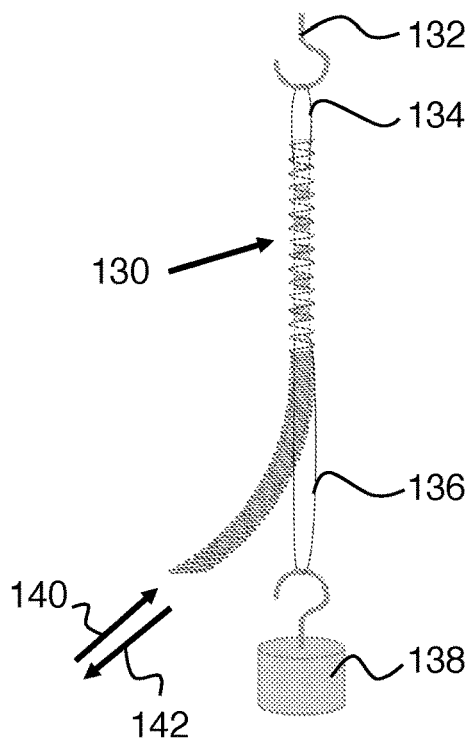
FIG. 1E shows a calibration setup for a fiber Bragg grating sensor.

To measure forces on the chordae, the FSN 130 was calibrated using known weights as shown on FIG. 1E. With one end of the FSN 130 fixed on a stand 132 with a suture 134, weights 138 were applied to the other end of the FSN 130 with a suture 136 to apply known calibration forces. The shift in reflected wavelength is linearly proportional to the strain on the FSN 130, which is linearly proportional to the applied force. Therefore, we can find a linear calibration equation that outputs the force value on the FSN based on the wavelength shift from strain. The wavelength shifts were measured using an optical interrogator (Optical Sensing Instrument si255, 1 kHz sampling rate, Micron Optics Inc., Atlanta, GA, USA).

Figure 1F:
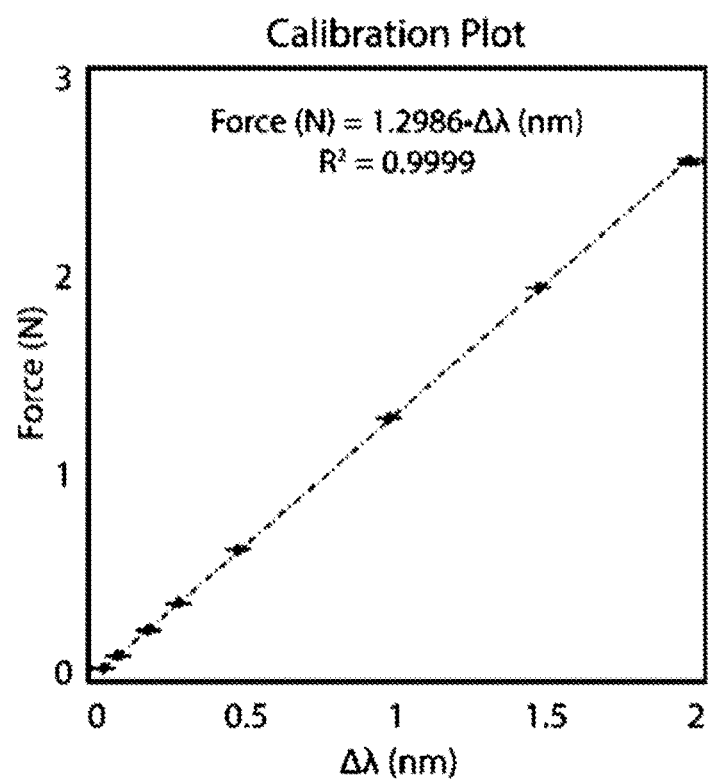
FIG. 1F shows an exemplary fiber Bragg grating sensor calibration.

FIG. 1F demonstrates how force and wavelength are related, which is also described by the following equation:

$$\Delta\lambda = \left(\frac{K_\varepsilon}{A_{fiber}E}\right)F_{weight} + K_T\Delta T \quad (2)$$

where $\Delta\lambda$ is the wavelength shift, $K_\varepsilon$ is the constant for mechanical strain, $F_{weight}$ is the force applied to the FBG sensor, $A_{fiber}$ is the cross-sectional area of the fiber, E is Young's modulus of the fiber, $K_T$ is the constant for temperature, and $\Delta T$ is the change in temperature. As shown in Eq. (2), temperature influences wavelength as well as force. Since we are primarily interested in force while the temperature ideally remains constant during experimentation, we treat temperature as a source of error.

To quantify the magnitude of temperature error on the FSN, they were subjected to temperature changes using a halogen light source and thermocouple to measure temperature changes accurately. We found that at the temperatures and force ranges typically found in the testing environment, the effect of temperature is very small compared to the force: a 1° C. temperature change is equivalent to approximately 0.01 N of force. To minimize error due to temperature fluctuation, temperature of the testing environment was tightly controlled and held constant at 37° C.±0.2° C., corresponding to a maximum error in the force measurement ranging between 0.2% for the largest chordae being measured to 4% in the smallest chordae measured. The strain sensitivity of our sensors was tested using an Instron 5848 Microtester (Illinois Tool Works Inc., Norwood, MA, USA) with a 20 N load cell and found to be less than the reported 0.1 µstrain. We also tested the accuracy and sensitivity of our calibration translating measured strains into forces. The accuracy was found to be approximately 3% and the sensitivity 0.01 N, both tested using forces less than or equal to 2 N given that this was the relevant range for this study. Because all forces measured in the mitral valve experiments are relative to the native baseline preload on the chordae, the FBG sensors were zeroed immediately prior to data collection during experimentation, thus mitigating accuracy errors.

B2a4) Error Estimation

Mismatch between the stiffness of the sensors and the native chordae tendineae is a source of measurement error using this technology, as with other strain gauge technologies. If the chordae tendineae are mechanically coupled and instrumented chordae are notably stiffer than uninstrumented neighboring chordae, the instrumented chordae would carry a disproportionate fraction of total force. However, we posited that our technique of replacing only a small segment of the chordae tendineae with the sensor could help mitigate measurement error to some degree, as the majority of the chordae tissue (with its native viscoelastic material properties) remains intact in the instrumented state. To assess whether this technique does attenuate the differences in stiffness between chordae tendineae and the optical fibers, we performed Instron tensile testing to compare load versus extension between an instrumented and uninstrumented chordae.

Figure 2:
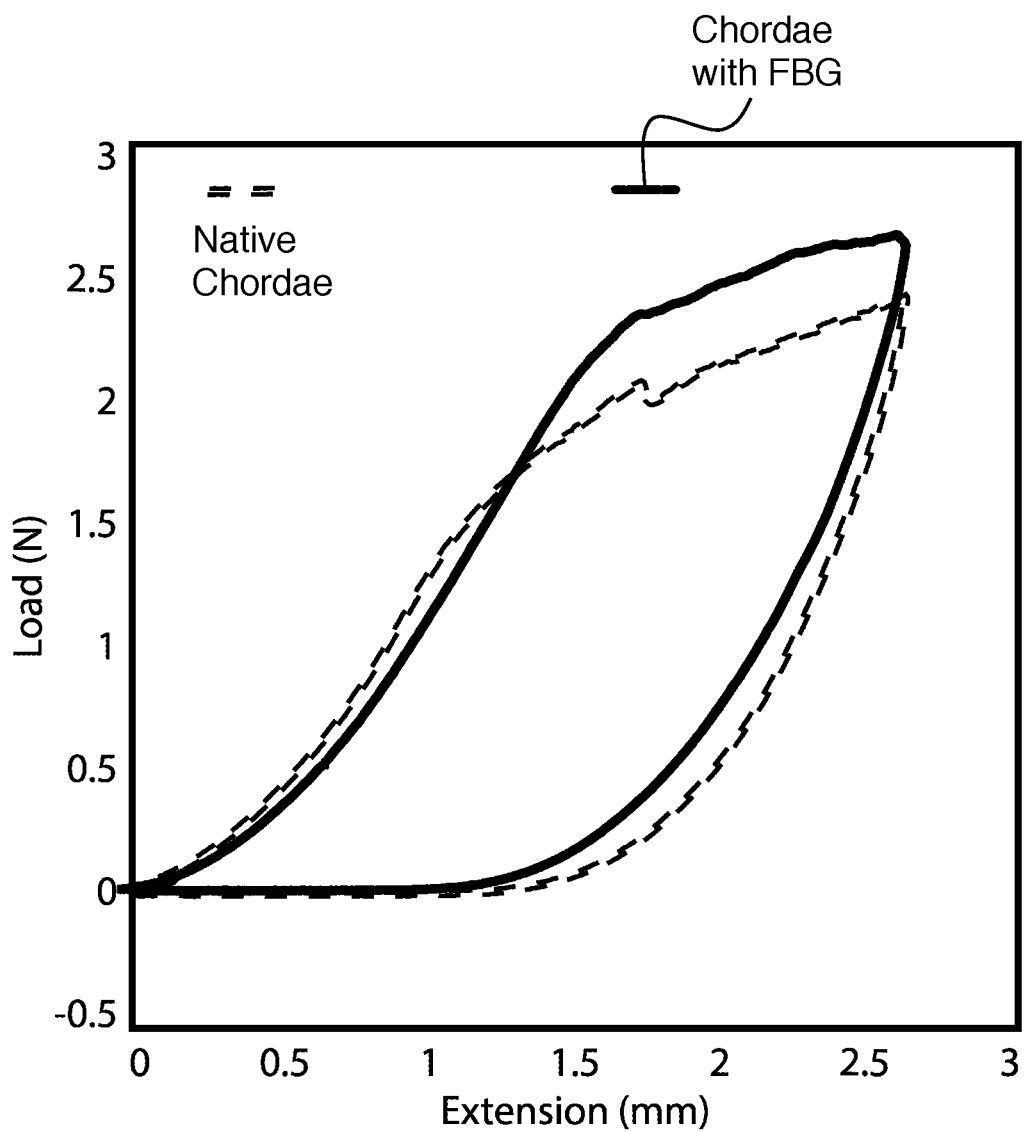
FIG. 2 shows load-extension curves for a native chordae tendineae and for a chordae tendineae having a fiber Bragg grating sensor.

We measured primary chordae, as they are thinner and shorter than secondary chordae and more likely to be affected by potential changes in stiffness due to sensor instrumentation. Preconditioning occurred at 1 mm/s to 5% strain for 5 cycles, adapted based on existing protocols for measuring chordae tendineae mechanical properties. The chordae were then subjected to 5 cycles of 20% strain at 1 mm/s (at which point the stress versus strain cycle was repeatable) and the final cycle was plotted (FIG. 2). Load versus extension was plotted here rather than the more traditional stress versus strain in order to more accurately compare how differences between the two conditions would impact the validity of the gauge readings when translating the FBG measurements to load on the chordae. This plot demonstrates that instrumented and uninstrumented chordae tendineae display similar slopes (i.e. stiffness) at each stage of the loading and unloading cycle, particularly at points within the load range we observed most force measurements to reside (between 0 N and 1.5 N).

In addition, instrumented chordae maintain the classic hysteresis loop (indicating lost energy in the loading cycle) that is associated with biologic, viscoelastic materials. Based on the results of this single pilot experiment to investigate tissue stiffness with and without the sensor, our technique of replacing only a small segment of chordae with the sensor preliminarily appears to help preserve the native stiffness of the instrumented chordae tendineae, which may minimize measurement error due to alternations in chordae material properties following sensor implantation. Furthermore, the fact that the tissues bracketing each chordae (the leaflets and the papillary muscles) are not rigid, but compliant, could help attenuate this error somewhat as well. As a result of this compliance, individual chordae can stretch relatively independent of each other and small changes in stiffness may result in changes in extension of that particular chordae, but might not significantly increase the overall force experienced by this chordae from coupling. As a result, small differences in stiffness of instrumented chordae may not propagate to an equally significant difference in force experienced by the instrumented chordae due to the mitigating effect tissue compliance has on mechanical coupling of chordae. Whether the effect of tissue compliance overcomes the effect of stiffness would likely vary depending on specific circumstances, and other researchers using similar sensing systems should verify that their particular setup minimizes error to an appropriate degree.

B2b) Left Heart Simulator

We designed a left heart model using computer-aided design software (Fusion 360, Autodesk Inc., San Rafael, CA, USA) and prototyped the device using additive manufacturing and machining technologies. The 3D-printed left heart chamber (Carbon M2, Carbon3D Inc., Redwood City, CA, USA) was mounted to a programmable pulsatile linear piston pump (ViVitro Superpump, ViVitro Labs, Victoria, BC, Canada) with the ability to generate physiologic conditions using the pump controller and software (ViVitest Software, ViVitro Labs). The heart simulator was also outfitted with ventricular, aortic, left atrial, and coronary pressure transducers (Utah Medical Products Inc., Midvale, UT, USA), electromagnetic flow probes in the aortic and mitral positions (Carolina Medical Electronics, East Bend, NC, USA), as well as a coronary flow probe (TS410 with 5PXN probe, Transonic Systems Inc., Ithaca, NY, USA).

The linear actuator piston attaches to the ventricular chamber of the heart simulator with a modified pump-head attachment; the attachment uses a silicone membrane to separate the working fluid within the pump from the test fluid, protecting the pump from contamination and damage. We used 0.9% normal saline as a test fluid to ensure proper transduction of the electromagnetic flow meters.

A viscoelastic impedance adapter (ViVitro Labs), which consists of a 0-120 mL source air compliance chamber, a 0-60 mL output air compliance chamber, and a 200 dyne·s/cm$^5$ fixed resistive element, was also outfitted to the heart simulator to reduce noise and generate more physiologic waveforms. In these experiments, we filled the source chamber with 100 mL of air and the output chamber with 50 mL of air. Compliance chambers in the aortic root and peripheral aortic position, with 500 mL total air volume each, were used to tune the waveform. Fluid from the venous reservoir enters the left atrial chamber via gravity, passes through the porcine mitral valve and into the ventricular chamber. The piston pressurizes the ventricular chamber, and fluid is ejected through the left ventricular outflow tract. After passing through the aortic flow probe and a mechanical aortic valve (29 mm St. Jude Regent, Abbott Laboratories, Chicago, IL, USA), test fluid flows into the aortic root compliance chamber through a model aortic root and then into the aortic compliance assembly. Next, the test fluid is routed through a heat-exchanger attached to an immersion circulator bath (PolyStat 3C15, Cole-Parmer, Vernon Hills, IL, USA) to keep the test fluid at 37° C., followed by a peripheral resistance throttle valve (ViVitro Labs), and finally back into the venous reservoir. To validate the system at baseline, a 28 mm leak-less disc valve (ViVitro Labs) in the mitral position was used.

The pump was programmed to generate an effective stroke volume of 70 mL/beat at 70 bpm, as measured by the flow meter. Next, peripheral resistance and compliance were titrated to generate a mean arterial pressure of 100 mmHg (systolic 120 mmHg, diastolic 80 mmHg) whilst keeping cardiac output at 5 LPM. A waveform complying with ISO 5840 standards for in vitro valve testing was used. The pressure transducers and flow meters were zeroed prior to every trial, and the baseline valve was reinstalled frequently between experimental trials to verify no drift had occurred.

B2c) Sample Preparation

Porcine hearts were obtained from a local abattoir and the mitral valves were excised, being careful to preserve the annulus, leaflets, and chordae. Some tertiary chordae attached to the ventricular wall did have to be cut while dissecting the valve, but all primary and secondary chordae were preserved. Only valves with intercommissural distances between 30-34 mm were used, and hearts with aberrant papillary muscle anatomy were excluded. A total of five valves were prepared and tested. A small cuff of left atrium was left in place and used to suture the mitral valve apparatus to a 3D-printed elastomeric polyurethane annular sewing plate (Carbon 3D) designed to fit between the left atrial and left ventricular chambers within the simulator. We attached the valve to the sewing ring using a cuff of left atrium rather than the annulus itself to better preserve native annular motion. The sewing ring itself was D-shaped to mimic the native mitral annulus, and the elastomeric material was chosen because it more closely matched the natural elasticity of the heart and held suture securely without tearing. Sewing rings were sized slightly larger (approximately 4 mm) than the native annulus of each valve to allow for an adequate cuff of left atrium attaching the valve apparatus to the elastomeric sewing ring and to prevent the sewing rings from restricting native annular motion. Importantly, because the native annulus is not rigidly attached directly to the sewing ring, its native motion and geometry are preserved, and it is free to conformationally change from saddle shape to flat during systole and diastole, respectively. Septolateral and transverse dimensions are also free to dynamically change throughout the cardiac cycle. 3D echocardiography was used to properly verify physiologic annular motion. We used six to ten interrupted 2-0 braided polyester horizontal mattress sutures to tack the valve in place on the sewing ring for proper alignment. Next, a hemostatic suture line was used to attach the left atrial cuff to the underside of the sewing ring more securely using a continuous running 2-0 polypropylene suture; this suture line was locked to avoid a purse-string constriction effect resulting in an inadvertent restrictive annuloplasty. The papillary muscles were sewn to molded silicone papillary muscle holders using four interrupted, pledgeted, 2-0 braided polyester horizontal mattress sutures per papillary muscle. These sutures were carefully placed to avoid deforming or entangling any chordae insertion points. The papillary muscle holders were affixed to the ends of carbon fiber rods instrumented through a spherical compression gasket to allow movement in the x, y, and z axes.

B2d) Implementation of the Sensing Unit

The annular plate with valve attached was secured in the left heart simulator. The force-sensing neochordae were passed through the carbon fiber rods that also served to position the papillary muscles using a modification of the Seldinger technique, allowing for quick sensor placement taking 5-10 minutes per chordae. We obtained 50 cm 14-gauge needles and sharpened them to a point. First, the needle was passed inferiorly through the papillary muscles—precisely at the insertion point of the chordae to be instrumented—and then passed through the silicone papillary muscle holders and carbon fiber papillary muscle positioning rods. Next, the sensors were passed superiorly through the needle until the sensor tip protruded through the proximal end of the needle. Holding the sensor fiber in position, the needle was carefully retracted superiorly over the sensor, leaving only the sensor passing through the papillary muscle, silicone papillary muscle holder, and carbon fiber positioning rod. The sensor was adjusted to the correct position relative to the chordae being instrumented by pulling superiorly or posteriorly and then locked into place. To lock the fibers into place without crushing them, we attached small segments of latex tubing to the proximal ends of the carbon fiber positioning rods, which the fibers also passed through. Plastic tubing clamps were carefully snapped into place once the fibers were in the correct position to prevent them from migrating during testing; the soft latex tubing not only cushioned the fibers to prevent crushing but also created a watertight seal. With the FSNs in the appropriate position, they were attached to the chordae of interest with PTFE suture, with the FSN being flanked on each side by a suture sewn to the respective chordae. To prevent the sensors from slipping, we first passed suture through the chordae, wrapping the suture around the chordae before securing it with a square knot. The sutures sewn to the chordae were then wrapped around the force-sensing neochord, taking care to ensure the suture was appropriately locked within one of the suture-locking grooves, and then secured with a series of square knots. Once attached, the segment of chordae between the sutures was cut, so that the force-sensing neochord transmitted the full load of the chordae. This was repeated on all chordae of interest—in this case, several primary and secondary chordae on both anterior and posterior leaflets. Once the valve, papillary muscles, and FSNs were in place, the chamber was sealed and filled with 0.9% normal saline at 37° C. Once filled, the papillary muscles were positioned anatomically with adequate coaptation of the mitral valve as determined visually, with echocardiography, and real-time flow measurements; once fixed, movement of the papillary muscle positioning rods was minimized. The FSNs were zeroed to ensure only relative forces—above the native preloaded state of the chordae—were examined.

Figure 3:
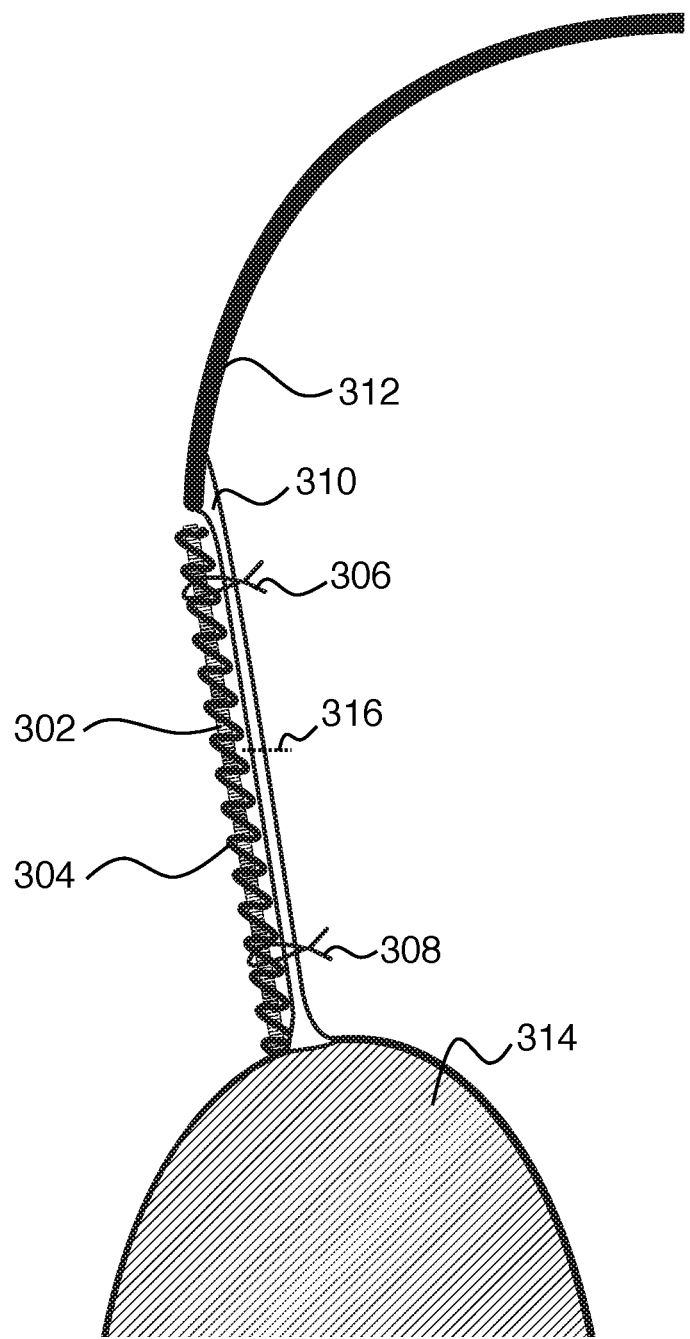
FIG. 3 shows attachment of a fiber Bragg grating sensor to a chordae tendineae.

FIG. 3 schematically shows this attachment process. Here 312 is a leaflet of a heart valve, 314 is a papillary muscle and 310 is a native chordae. The fiber Bragg grating sensor 302 is wrapped in a coil 304 as described above in connection with FIG. 1D. Sutures 306 and 308 are used to affix the sensor 302 to the chordae 310. Chordae 310 is then cut between the sutures, e.g., at cut location 316.

B2e) Data Acquisition and Analysis

After valves were mounted and FSNs were implanted, the system was filled with 37° C. normal saline, deaired, and allowed to run for 10 minutes prior to data collection. After 10 minutes, all sensors were zeroed and data collection began, which included pressure tracings, flow meter readings, and force readings from the instrumented chordae. Data was exported into MATLAB (R2018a, Mathworks Inc., Natick, MA, USA) for plotting and into R for statistical analysis (R 3.6.0. with Jamovi 0.9.6.9 user interface). Continuous variables are reported as mean±SD unless otherwise noted. Non-parametric, paired-samples Wilcoxon tests were used to compare variables between the baseline and hypertensive conditions. A p-value of <0.05 was considered statistically significant.

B3) Results

Figure 4A:
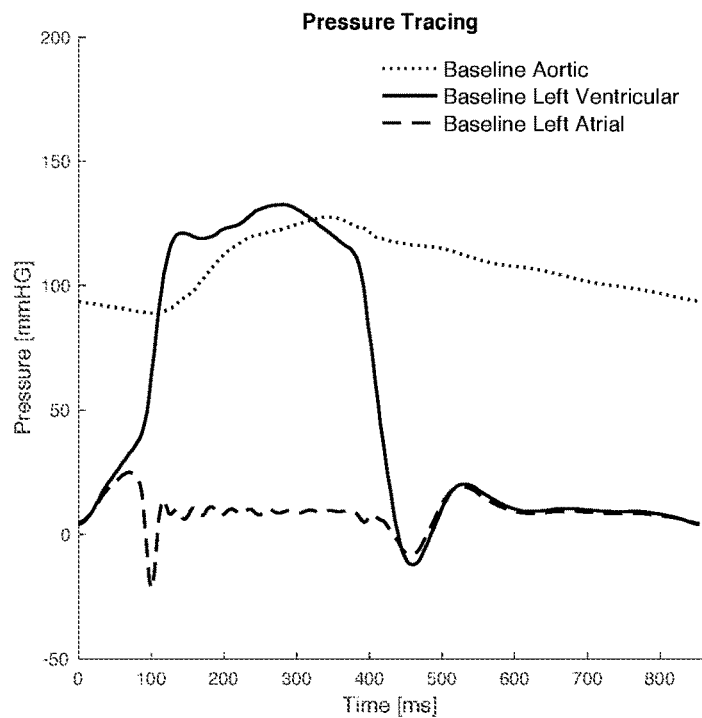
FIGS. 4A-D show measured flow and pressure in a left heart simulator.
Figure 4B:
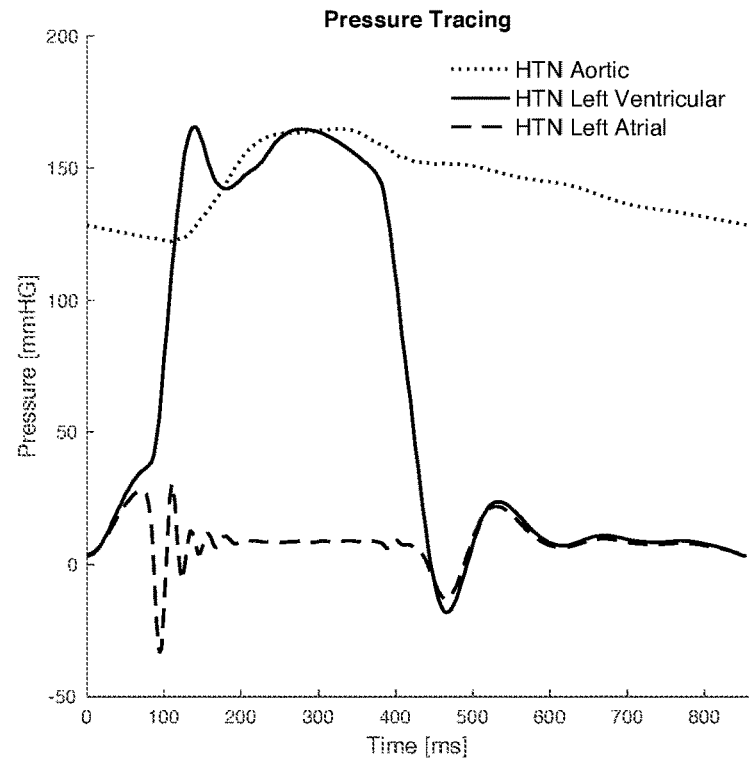
Figure 4C:
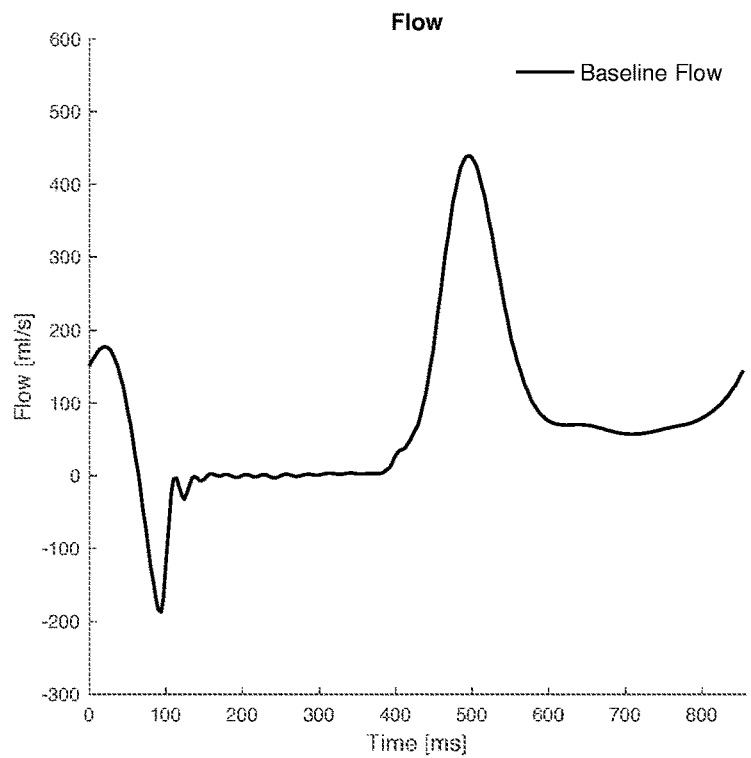
Figure 4D:
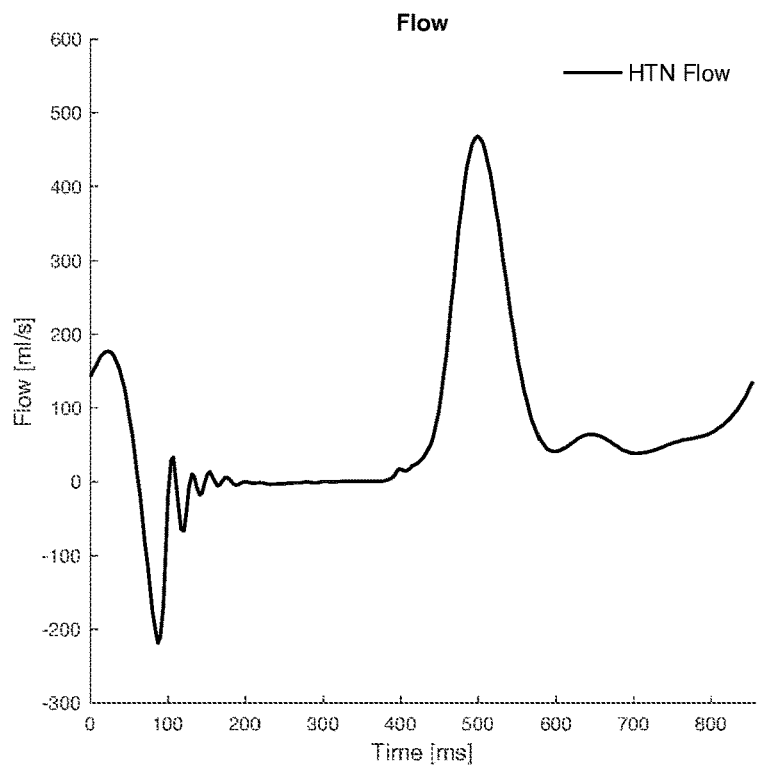

The 3D-printed left heart simulator generated physiologically representative pressure and flow waveforms, which are shown in FIGS. 4A-D. At baseline (FIGS. 4A and 4C), mean arterial pressure was 99.41±0.96 mmHg, systolic pressure was 120.79±1.07 mmHg, and diastolic pressure was 78.75±1.84 mmHg. FIGS. 4B and 4D show corresponding results for a hypertensive (HTN) condition. Implantation of FSNs onto mitral valve chordae reliably generated high-fidelity force data with no obvious adverse effects on valve function or coaptation, with regurgitant fractions within normal ranges (7.07±2.25%), most of which was closing volume. Echocardiographic data also verified normal leaflet and subvalvular apparatus kinematics. Up to six FSNs were implanted simultaneously on independent chordae with successful force measurement and no interference between sensors.

Figure 5A:
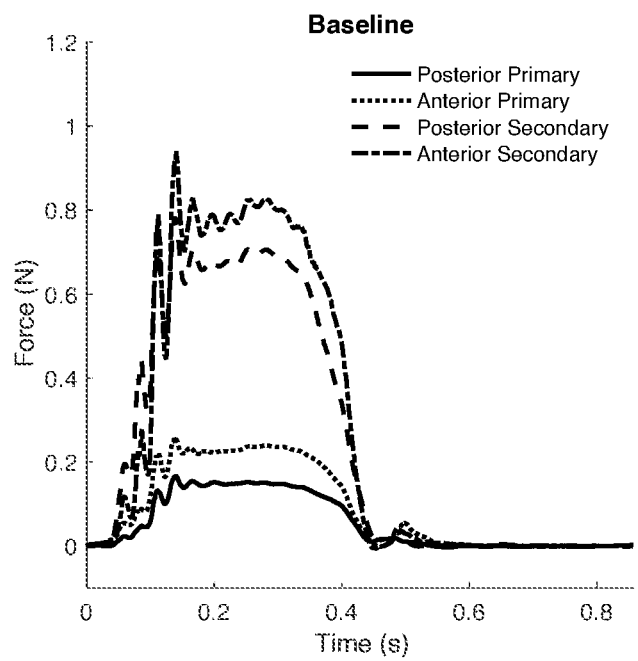
FIGS. 5A-B show measured in situ chordae tendineae forces from the left heart simulator.
Figure 5B:
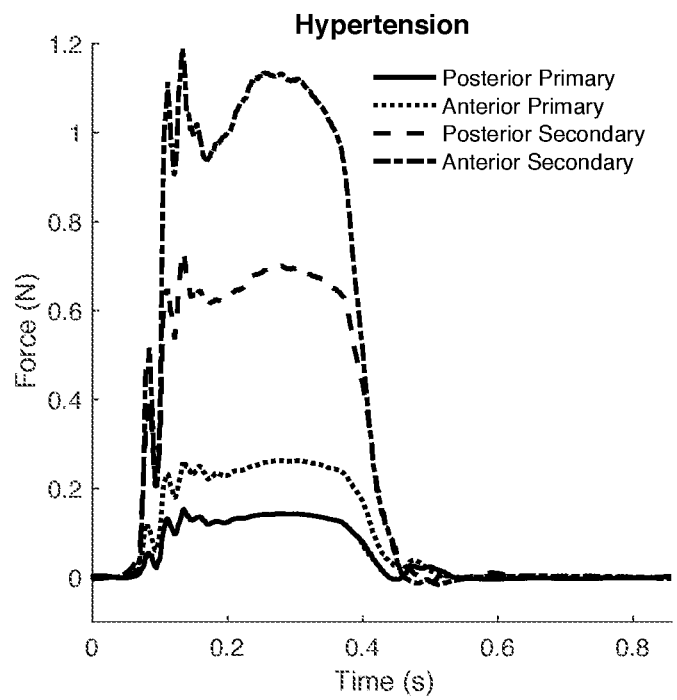

Chordae tendineae forces are shown graphically in FIGS. 5A-B for baseline and hypertensive conditions, respectively. Our chordae force measurements are in agreement with reported values from the literature using various sensing techniques. To verify functionality of the FSNs, the system pressure was increased to replicate hypertensive conditions with a mean arterial pressure of 135.78±1.90 mmHg, systolic pressure of 158.21±2.94 mmHg, and diastolic pressure of 114.06±2.24 mmHg. Chordae tendineae forces in all positions were significantly elevated in the hypertensive condition. Specifically, forces at baseline and hypertensive conditions for anterior primary chordae were 0.17±0.08 N vs. 0.23±0.11 N (p=0.004). Posterior primary chordae tendineae forces at baseline were 0.12±0.06 vs. 0.14±0.07 N (p=0.013) during hypertensive conditions. For anterior secondary chordae, baseline forces were 0.74±0.22 vs. 1.02±0.38 N during hypertensive conditions (p=0.021) and 0.60±0.26 vs. 0.78±0.30 N (p=0.026) for posterior secondary forces at baseline and during hypertensive conditions, respectively. Forces on secondary chordae appeared to increase to a higher degree in response to increased pressure as opposed to primary chordae, which were less impacted. Early trials did have isolated instances of the FSNs becoming detached from the chordae, which was solved by increasing the size of the PTFE suture or using a figure-of-eight attachment suture on the chordae prior to tying the FSN in place. None of the FSNs, once implanted, failed or ruptured during testing.

B4) Discussion

The results of our study demonstrate that Fiber Bragg Grating (FBG) optical sensors can be successfully incorporated into devices to measure multiple simultaneous mitral valve chordae tendineae forces with a high degree of sensitivity and reproducibility, while overcoming some limitations of earlier technology. In addition, the small footprint of FBGs allows forces on multiple chordae to be simultaneously measured, which is challenging with bulkier sensors. In addition, their small size and weight also minimizes the impact the sensor has on the structures being measured. Furthermore, FBG-based sensors are waterproof and robust in the tensile direction of force measurement. Electromagnetic fields do not interfere with FBG measurements, allowing them to be used in a variety of clinical environments, including during MRI.

In this work it is important to note that a planar annular model was used for simplicity, as our aim was to focus primarily on the measurement technology. As a multitude of studies on various annular conformations have clearly demonstrated, annular geometry and material properties exert pronounced effects on chordae tension and valvular function. The sensing technology we describe can be used in a range of other in vitro and in vivo annular models, and is an important future step.

While FBGs overcome some issues that have faced prior measurement strategies, they are not without limitations. For one, the associated equipment is costly, and the individual fibers are expensive. Additionally, fabrication requires a multiple-week lead time and calibration can be time-intensive. We have begun using an Instron 5848 Microtester (Illinois Tool Works Inc., Norwood, MA, USA) with a 20 N load cell to perform automated tensioning cycles to increase calibration accuracy and speed. While silica-based FBGs have tremendous tensile strength, they are prone to breaking if bent past their maximum radius of curvature or if crushed (in a vessel clip, for example, which we experimented with unsuccessfully in lieu of sutures to make the mounting process quicker). The peak wavelength measurements can widen or split when the sensors are subjected to non-uniaxial loading; this is particularly important for the proposed technique because it necessitates careful attachment to the chordae to ensure the FBG is pulled only along its longitudinal axis. They are also prone to a "whip" phenomenon if they are not secured proximally, which is why we chose to run the fibers within the papillary muscle mounting rods and not freely floating in the ventricular chamber. In addition, naked fibers can be difficult to see, so inadvertently cutting them along with the chordae being instrumented can occur and is a costly mistake. Though we are working to manufacture shorter fibers that replace a smaller fraction of the native chordae (and thus better retaining the native chordae's viscoelastic response), the current disparity in stiffness between the native and instrumented chordae can result in measurement error and represents an important limitation in our technique. Polymer-based fibers will solve many of the limitations of silica-based FBGs, including more closely matching the material properties of native chordae tendineae to reduce error due to the sensor replacing a segment of native chordae. These polymer-based FBGs have been developed in several laboratories globally but are not yet available commercially. In addition, polymeric FBGs will be substantially more robust and flexible, allowing for further development of novel biological and clinical sensing systems.

B5) Conclusions

Using Fiber Bragg Grating optical strain gauges, a novel device created to measure mitral valve chordae tendineae tension was successfully developed, tested, and validated. This new force-sensing device, with its small physical footprint and high fidelity, allows for measurement of multiple chordae simultaneously with minimal interference on leaflet or chordae kinematics.

C) Variations

C1) Improved FBG Mechanical Configuration

In a preferred embodiment, the FSNs are manufactured by injecting a urethane compound around an FBG core encased in heat shrink tubing. In another embodiment, silicone or any other suitable compound which transitions from a liquid to solid state is used instead or in addition to the urethane. Heat is then applied to the tubing prior to the compound setting in order to shrink around the FBG. In another embodiment, the tubing does not shrink due to heat exposure and no heat is applied. Optionally, a protective coil sheath with embedded suture gripping structures may also be included around the FBG core and inside the tubing for added protection. Once the compound is set, it can be used for suture attachment—the urethane grips the FBG without sliding so when sutures are places proximal and distal to the FBG sensor in the urethane, they can be put in tension to strain the sensor. The FSN thus acts much like a chordae tendinae with suture location up to the discretion of the operator. The fiber distal to the distal attachment point is terminated so that the sensor can be implanted within the mitral valve apparatus. The heat shrink tubing aids in decreasing the likelihood of suture pull-out. The urethane acts to distribute forces more evenly while preventing cracking of the FBG due to bending and twisting, which is a significant problem with other methods. To correlate strain to force, an automated force calibration procedure, as described below can be used.

In a preferred embodiment, to correlate measured strains to forces, FBGs were individually calibrated using a tensile testing machine. Preferably, the tensile testing machine is an Instron Microtester (Norwood, MA) with a load cell between 2 and 100 N. In this embodiment, the sensors were tensioned at 0.8 mm/min from 0 N to 2 N, and then at −0.8 mm/min to return to the initial state. This pattern was repeated three times while strain data was simultaneously collected from the FBGs. Alternatively, the sensors are tensioned at 1 N/min. The 0-2 N range was chosen as representative of the forces the FBGs encounter during experiments, though the range can be adjusted depending on the experimental purpose. The calibration of the fibers maintained a sensitivity of approximately 0.01 N during calibration. For each sensor, a least squares regression is used to correlate the FBG strain data to the Instron load data.

Figure 6A:
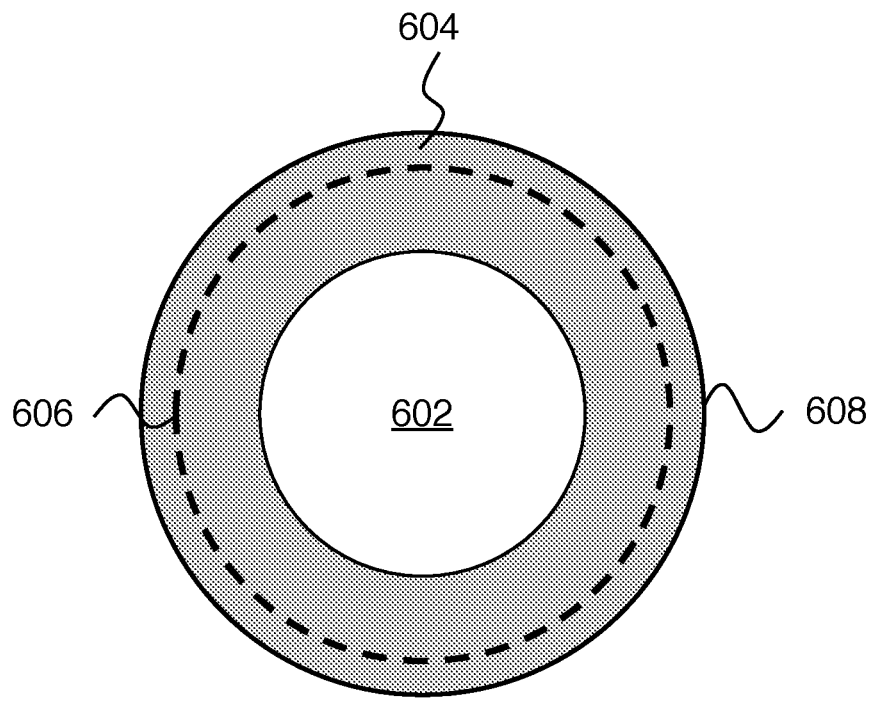
FIGS. 6A-B show a preferred configuration for a fiber Bragg grating sensor.
Figure 6B:
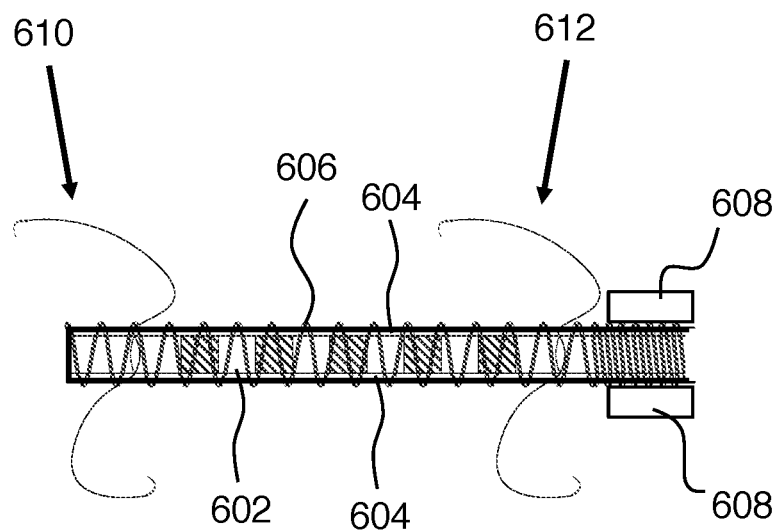

FIGS. 6A-B schematically show an example of this preferred sensor configuration. FIG. 6A is a cross section view and FIG. 6B is a corresponding side view. Here 602 is the fiber Bragg grating sensor, 604 is the urethane shell, 606 is the coil and 608 is the outer heat shrink tubing, all as described above. The suture locations are left uncovered by heat shrink tubing 608 as shown on FIG. 6B so that coil 606 can provide suture locking grooves.

C2) Large-Animal In Vivo Results

Previous methods of FBG strain gauge manufacturing for chordal force evaluation ex vivo resulted in a significant fault that prevented their successful in vivo use: the strain gauges were not sufficiently durable to withstand the extra stress and complications of large animal (or human) implementation. During ex vivo use we frequently had even small bending of the strain gauge result in cracking of the fragile glass fiber. However, while replacing these broken FBGs was possible ex vivo, it would be far more difficult and time-consuming in vivo, ultimately resulting in an extended time on bypass or a complete loss of data if the breaking occurred after bypass had concluded.

Figure 7A:
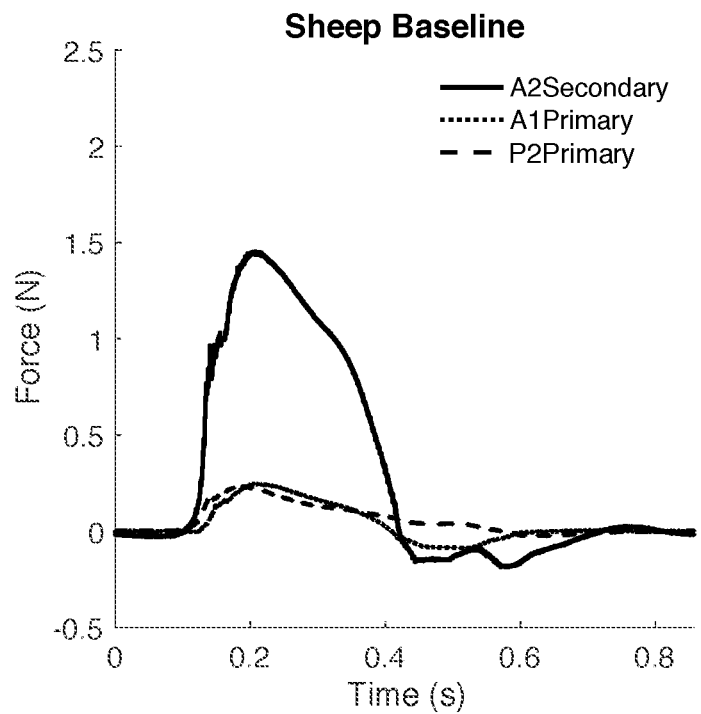
FIGS. 7A-B show measured in vivo chordae tendineae forces from a sheep.
Figure 7B:
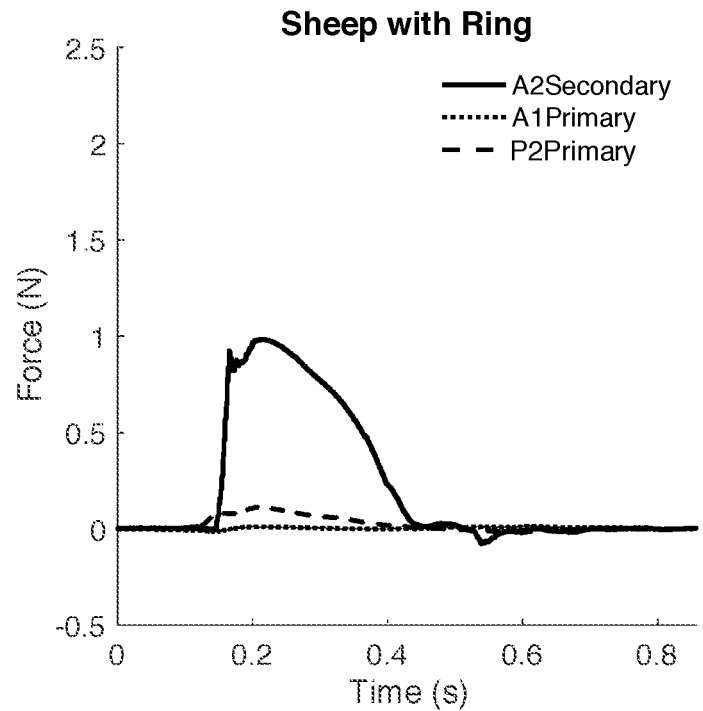
Figure 7C:
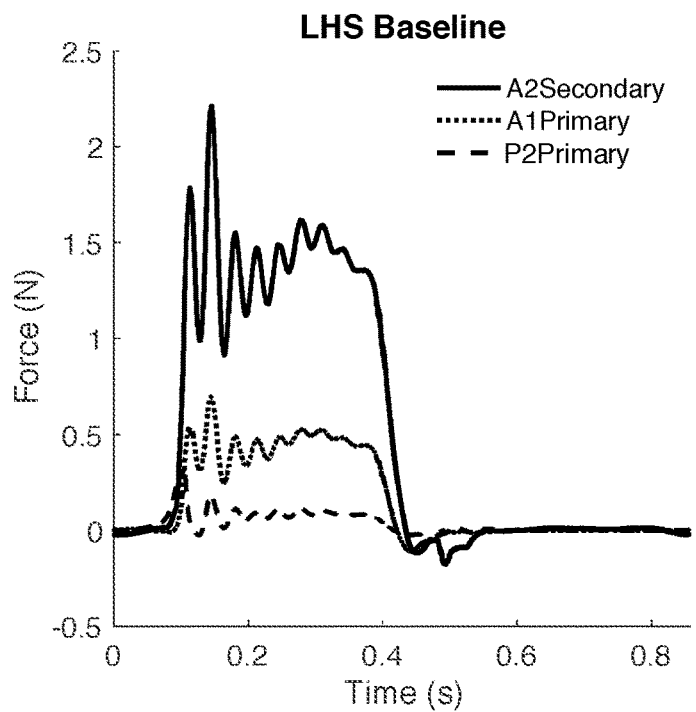
FIGS. 7C-D show measured in situ chordae tendineae forces from the left heart simulator for comparison to the results of FIGS. 7A-B.
Figure 7D:
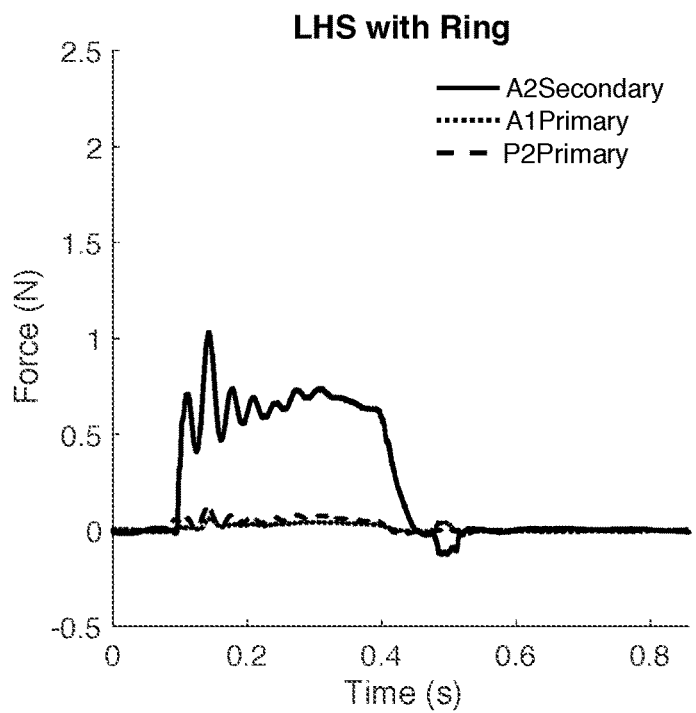

These considerations prompted development of the sensors of section C1. These strain gauges are far more resilient with the ability to withstand significant bending and force in all directions, thus allowing for implementation in vivo without breaking. FIGS. 7A-D present the results of an in vivo study made possible by these more resilient strain gauges. FIGS. 7A-B show the forces measured on three chordae tendineae of a sheep experiencing natural mitral regurgitation—(FIG. 7A) baseline and (FIG. 7B) with an annuloplasty ring used to restore proper coaptation of the valve. FIGS. 7C-D then show the same valve explanted and mounted in the ex vivo left heart simulator to repeat the force measurements, both with and without the annuloplasty ring. Both the left heart simulator and in vivo results show similar decreases in chordal forces when coaptation is restored with the annuloplasty ring. In addition, we hypothesize that the smoother in vivo force tracings compared to the ex vivo results is due to the motion of the papillary muscles over the course of a cardiac cycle, which likely helps to cushion the sharp increase in stress on the chordae at the start of systole. This difference further stresses the importance of in vivo analysis on chordal forces due to the high complexity of the heart that cannot be fully captured in an ex vivo simulation.

C3) Clinical Applications

Figure 8:
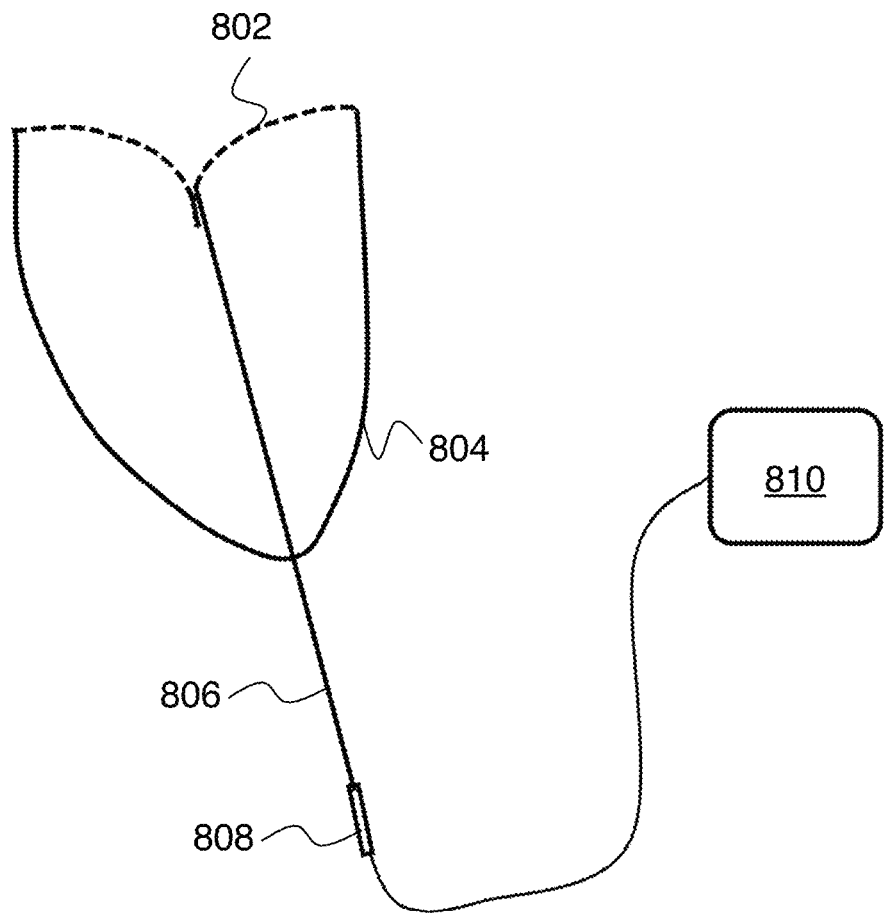
FIG. 8 schematically shows use of a fiber Bragg grating sensor to sense chordae tendineae forces during surgery.

The preceding description relates to use of FBG sensors for measuring chordae forces in research applications. It is also possible to use FBG sensors in clinical applications. FIG. 8 schematically shows an example. Here 802 is a valve leaflet of a heart 804. A prosthetic neochordae 806 is affixed to leaflet 802. An FBG sensor 808 is in-line with the prosthetic neochordae 806 to provide a measurement of tension on neochordae 806 via display 810. The situation shown on FIG. 8 could occur during heart surgery to implant neochordae 806, where monitoring the tensile force on the neochordae during the surgery could be valuable, especially right before affixing neochordae 806 to heart wall 804. Neochordae force sensing during surgery using electrical strain gauges has been considered in the art by Grinberg et al. (Scientific Reports, March 2019, 9:4677). It is expected that art workers would be able to adapt such surgical procedures to use FBG sensors as described herein.

Accordingly, an embodiment of the invention is a method of heart valve surgery, where the method includes the steps of:

1) providing a prosthetic artificial neochordae;
2) anchoring a heart valve leaflet to the heart wall with the prosthetic artificial neochordae with a surgical procedure; and
3) providing a fiber Bragg grating sensor affixed to the prosthetic artificial neochordae during the surgical procedure and configured to measure tensile force on the prosthetic artificial neochordae. Here the tensile force on the prosthetic artificial neochordae is monitored during part or all the surgical procedure using the fiber Bragg grating sensor. Note that the FBG sensor is not permanently affixed to the implanted prosthetic neochordae. Instead it is removed from the prosthesis in a late stage of the surgical procedure. For example, in the situation shown in FIG. 8, cutting the prosthetic neochordae to an appropriate length will effect this removal of the FBG sensor from the implanted prosthetic neochordae.

The invention claimed is:

1. A method of measuring chordae tendineae forces during operation of a heart valve, the method comprising:
   providing a fiber Bragg grating (FBG) force sensor having a first attachment point and a second attachment point, wherein the FBG force sensor is configured to sense tensile force applied to pull the first and second attachment points apart;
   affixing the first attachment point of the FBG force sensor to a chordae tendineae at a first location on the chordae tendineae;
   affixing the second attachment point of the FBG force sensor to the chordae tendineae at a second location on the chordae tendineae;
   wherein a sensor distance between the first and second attachment points is substantially the same as a chordae distance between the first and second locations;
   severing the chordae tendineae between the first and second locations;
   performing force measurements with the FBG force sensor during operation of the heart valve connected to the chordae tendineae.

2. The method of claim 1, wherein the heart valve is a mitral valve.

3. The method of claim 1, wherein the FBG force sensor is configured to provide a reflectance spectrum from which force is determined.

4. The method of claim 1, wherein the FBG force sensor is surrounded by a protective sheath.

5. The method of claim 4, wherein the protective sheath comprises a coil affixed to the FBG force sensor at the first and second attachment points and having a separation between adjacent coil loops sufficient to accommodate a suture.

6. The method of claim 4, wherein the protective sheath comprises a urethane shell disposed circumferentially around the FBG force sensor and bonded to the FBG force sensor.

7. The method of claim 6, wherein the protective sheath further comprises a coil disposed circumferentially around and in contact with the urethane shell.

8. The method of claim 7, wherein the protective sheath further comprises heat shrink tubing disposed circumferentially around and in contact with the coil along part of a length of the FBG force sensor.

9. The method of claim 8, wherein the coil has a separation between adjacent coil loops sufficient to accommodate a suture on a part of the FBG force sensor not covered by the heat shrink tubing.

10. The method of claim 4, wherein the protective sheath is configured to reduce non-tensile force on the FBG force sensor.

11. The method of claim 1, wherein the FBG force sensor comprises an optical fiber selected from the group consisting of: silica fibers and polymer fibers.

12. The method of claim 1, wherein a distance between the first and second attachment points is 10 mm or less.

* * * * *